United States Patent [19]

Huck et al.

[11] 4,182,448

[45] Jan. 8, 1980

[54] RECEIVER FOR DISPOSABLE SURGICAL SHARPS

[75] Inventors: Charles M. Huck, Oldwick; Charles R. Ashley, Clinton; Ina L. Williams, Somerville; Harvey B. Mandel, North Brunswick, all of N.J.

[73] Assignee: Ethicon, Inc., Somerville, N.J.

[21] Appl. No.: 929,065

[22] Filed: Jul. 28, 1978

[51] Int. Cl.² .................... A61C 17/02; B65D 73/00; B65D 85/24

[52] U.S. Cl. .................. 206/380; 206/63.3; 206/365; 206/382; 206/460; 206/813

[58] Field of Search ............. 206/380, 382, 363, 370, 206/63.3, 460, 470, 472, 473, 475, 484.1, 484.2, 486, 489, 803, 813

[56] References Cited

U.S. PATENT DOCUMENTS

| | | | |
|---|---|---|---|
| 1,310,729 | 7/1919 | Appelbee | 206/475 |
| 3,047,144 | 7/1962 | Wissel | 206/813 |
| 3,191,319 | 6/1965 | Waisgerber | 206/472 |
| 3,202,279 | 8/1965 | Czerkies | 206/470 |
| 3,389,784 | 6/1968 | Hendricks | 206/803 |
| 3,861,521 | 1/1975 | Bartz | 206/363 |
| 3,944,069 | 3/1976 | Eldridge | 206/460 |
| 4,015,708 | 4/1977 | Kelm | 206/472 |
| 4,046,254 | 9/1977 | Kramer | 206/370 |

Primary Examiner—George E. Lowrance
Attorney, Agent, or Firm—Wayne R. Eberhardt

[57] ABSTRACT

A receiver for disposing of used surgical sharps particularly needles and scalpel blades, comprising an adhesive-coated, rectangular backing panel having a cover panel and two matrix panels attached along the sides thereof. The matrix panels have cut-out windows of different sizes to accommodate the surgical sharps. In use, one matrix panel is removed and discarded while the other is folded over and secured to the adhesive-coated side of the backing panel. Used surgical sharps deposited in matrix panel windows are retained on the adhesive coating of the backing panel which forms the floor of the matrix window. When all matrix windows are used, or the surgical procedure is complete, the adhesive coated cover panel is folded over the matrix panel to seal the matrix windows and the sharps contained therein. Preferably, the cover panel is transparent to allow the sharps to be visually identified and counted after the receiver is sealed.

11 Claims, 3 Drawing Figures

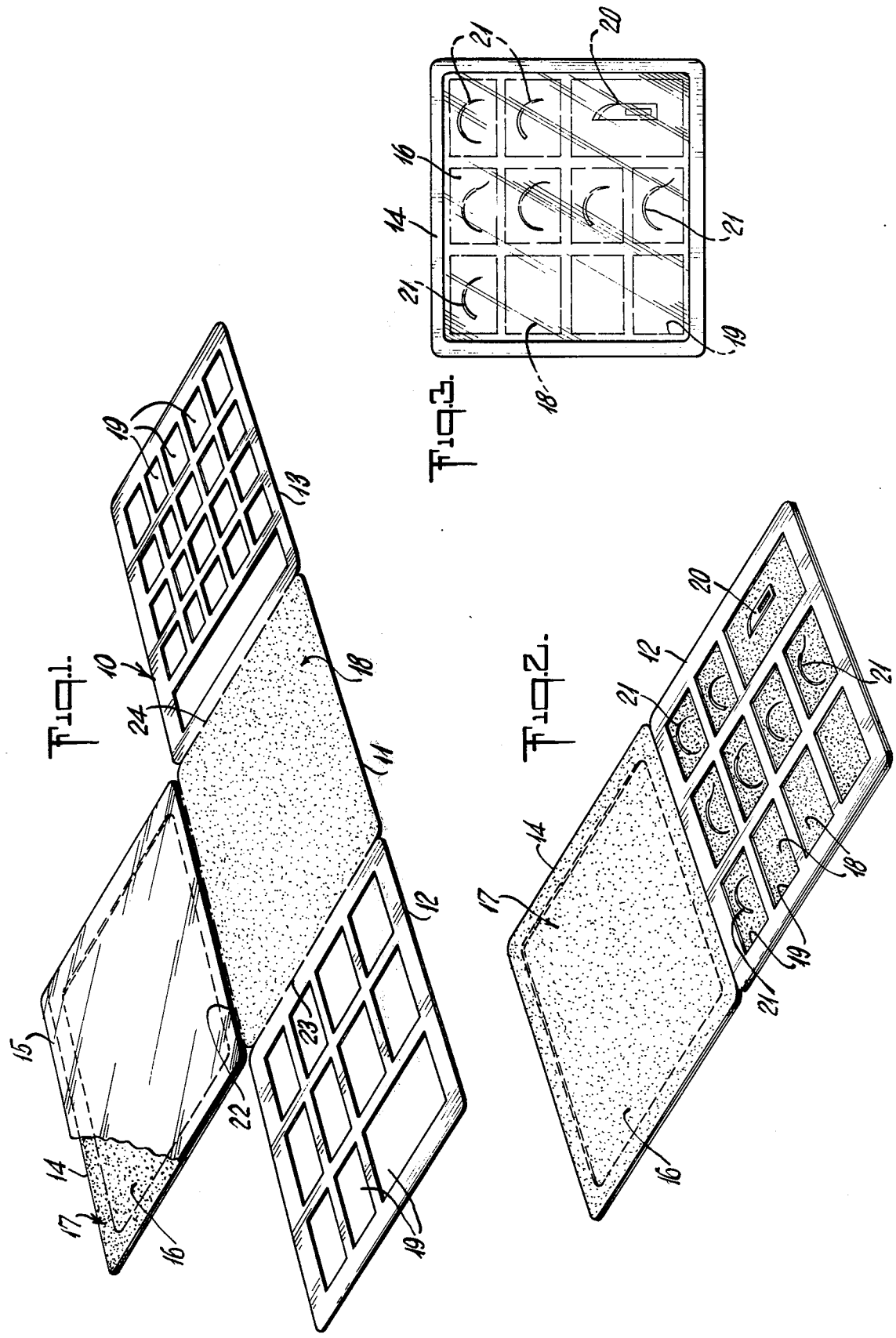

RECEIVER FOR DISPOSABLE SURGICAL SHARPS

BACKGROUND OF THE INVENTION

1. Field of the Invention

This invention relates to devices for receiving, storing, and disposing of small objects, particularly used and disposable surgical sharps.

2. Description of Prior Art

Modern surgical procedures often involve the use of disposable surgical implements including sharps such as needles and scalpel blades. Many surgical sutures are provided to the surgeon in short lengths with disposable needles attached to one or both ends by swaging or other means. Such armed sutures are preferred by surgeons because the needles are always new and sharp, and the attached needles cause less tissue disruption than occurs with an eyed needle.

Upon completion of a suturing procedure with an armed suture, the needle is cut or otherwise removed from the suture and discarded. Since some surgical procedures may involve 20 or 30 or more individual sutures, there may be a large number of needles to be accounted for and disposed of after the operation. In addition, there may be various disposable scalpel blades, hypodermic needles, lances, and the like which are also discarded after use.

Good surgical practice requires that all surgical implements used in a surgical procedure be accounted for upon completion of the procedure. To simplify this accounting procedure, various devices for receiving and disposing of needles and other small surgical implements have been proposed in the prior art. U.S. Pat. No. 3,944,069, for example, provides an adhesive coated pad upon which the needles may be deposited and which may be folded in half to enclose the needles after the operation. The pad of this patent, however, does not provide for organization of the discarded implements to facilitate counting, nor does it allow the discarded implements to be viewed or recounted once the pad is closed.

U.S. Pat. No. 4,008,802 describes a pad of resilient material having raised ridges through which needles can be inserted, with consecutively numbered zones to facilitate counting of the needles. Once filled, however, the pad is folded in half to enclose the needles and later verification of the needle count cannot be readily made.

It is accordingly an object of the present invention to provide a receiver for small, disposable surgical implements which automatically organizes the implements for counting, and which permits the discarded implements to be identified and recounted after the receiver is sealed. A further object of this invention is to provide a receiver which allows the user flexibility in adapting the receiver to accept a large number of small items or a lesser number of larger items. These and other objects of this invention will become apparent from the ensuing description and claims.

SUMMARY

The receiver of the present invention is constructed of paperboard or other thin, foldable material, and is preferably composed of four attached panels. A solid, central backing panel is coated with a pressure sensitive adhesive. Attached to the backing panel along one edge thereof is a cover panel which is also coated with a pressure sensitive adhesive and is preferably transparent over a major portion thereof. Attached along two other edges of the backing panel are two matrix panels having a plurality of surgical implement receiving window cut-outs. One matrix panel has a large number of small windows while the other matrix panel has a smaller number of larger windows. The matrix panels are perforated or otherwise weakened along the line of attachment to the backing panel to facilitate removal of either matrix panel.

In use, the surgeon or nurse selects one matrix panel according to the size of the surgical implements utilized in the particular procedure. The selected panel is folded over the backing panel and secured thereon by the pressure sensitive adhesive coating. The other matrix panel is detached from the backing panel and discarded.

The receiver is placed in a convenient location with matrix-panel side up and the cover open. Surgical needles, scalpel blades and other implements are discarded into the matrix windows as they are used, preferably with one item per window. The discarded items in the matrix windows rest on the backing panel and are held in place by the adhesive coating thereon. When all the matrix windows have been used, the cover of the receiver is folded over the matrix panel and secured by the adhesive coating on the surface of the cover panel. The surgical implements are thereby enclosed within the matrix windows and between the backing panel and the cover panel. The cover panel is preferably transparent to allow viewing of the enclosed surgical implements when the receiver is closed. Since the matrix has a finite number of windows, counting of surgical implements is simplified if care is taken to place only one implement in each window and to use all the windows before the receiver is sealed.

The cover panel and backing panel are preferably supplied with release papers covering the adhesive coating to prevent adhesion between stacked receivers. The release paper on the backing panel is removed when the selected matrix panel is folded over the backing panel, and the release paper on the cover panel is removed just before sealing the loaded receiver. Alternatively, the receiver may be supplied in a folded condition with the cover panel folded over the backing panel and a single release paper between the adhesive layers of the two panels. When the receiver is unfolded, the release paper is maintained on the cover panel and the backing panel is exposed and ready for attachment of the selected matrix panel. When the receiver is supplied in a folded condition, it is most convenient to fold both matrix panels in overlapping position on the nonadhesive coated side on the backing panel.

Loaded and sealed receivers are readily stacked, filed, and marked for identification, and may be retained as a permanent visual accounting record of the surgical sharps and small implements used and collected in any procedure.

DESCRIPTION OF DRAWINGS

FIG. 1 is a view in perspective of the four-panel receiver of the present invention.

FIG. 2 is a view in perspective of the receiver of FIG. 1 during use with one matrix panel removed and the other folded into position over the backing panel.

FIG. 3 is a plan view of the receiver after use with the cover panel closed.

DESCRIPTION OF PREFERRED EMBODIMENTS

FIG. 1 illustrates receiver 10 consisting of backing panel 11, left matrix panel 12, right matrix panel 13, and cover panel 14. Matrix panels 12 and 13 are foldably attached to backing panel 11 along lines 23 and 24 respectively, which are preferably perforated lines to facilitate the removal of the matrix panel which is not selected for use. Cover panel 14 is attached to backing panel 11 along fold line 22.

Backing panel 11 is coated with pressure sensitive adhesive 18 on the upper surface as illustrated. Cover panel 14 is also coated with a pressure-sensitive adhesive 17 on the upper surface as illustrated and is additionally provided with a release paper 15 to cover and protect the adhesive. As illustrated, cover panel 14 has a transparent insert 16 over an area corresponding to expanse of the windows 19 in matrix panels 12 and 13 to allow the contents of the used receiver to be viewed as hereinafter explained.

Matrix panels 12 and 13 have cut-out windows 19, with one panel preferably having a large number of small windows and the other panel having a lesser number of larger windows as illustrated. While in a preferred embodiment of the present invention, one matrix panel has at least ten windows and the other has at least twenty windows, the number, configuration, and arrangement of windows may be varied as desired.

Prior to use, the receiver is opened as illustrated in FIG. 1 and one matrix panel is selected for use while the other is detached from the backing panel and discarded. The selected matrix is folded over the adhesive coated side of the backing panel and adhesively secured thereto. FIG. 2 illustrates the receiver of FIG. 1 wherein matrix panel 13 has been detached and discarded, and matrix panel 12 has been folded into position over backing panel 11. Adhesive coating 18 of backing panel 11 now appears through the open windows of matrix panel 12 and provides an adhesive depository for discarded surgical sharps such as needles 21 and scalpel blade 20 illustrated in FIG. 2.

Surgical sharps are preferably deposited with one item per matrix window to facilitate later identification and counting. It is contemplated, however, that more than one item may be placed in each window, particularly if the larger windows are being used. One advantage of the present invention, however, is in providing the surgeon or nurse with an option to select a greater number of smaller windows if the particular surgical procedure will result in a large number of small sharps to be discarded. Thus, in such a procedure, the surgeon would select matrix panel 13 of FIG. 1 for use with the receiver and discard matrix panel 12.

When each window of the matrix panel has received a surgical sharp, release paper 15 is removed from cover panel 14 and the cover panel is folded forward over the matrix panel and adhesively secured thereto. Transparent insert 16 in cover panel 14 allows the enclosed sharps to be viewed for identification and counting. FIG. 3 illustrates a filled receiver with all sharps enclosed within the windows of matrix panel 12 and between backing panel 11 and cover panel 14.

The receiver of the present invention is conveniently die cut from a single piece of paperboard or similar stiff, foldable material. Fold lines 22, 23, and 24 may be impressed during the die cutting operation, and lines 23 and 24 may additionally be perforated for easy removal of the unneeded matrix panel. Transparent insert 16 is adhesively secured to the paperboard border of cover panel 14 and the surface of backing panel 11 and cover panel 14 including transparent insert 16 coated with a transparent, pressure sensitive adhesive. Release paper 15 may be transparent or opaque and be any of a number of silicone or polyethylene-coated papers which are well-known in the art for this application.

The receiver of the present invention is preferably supplied in a sterile package ready for use in the operating room. For convenience of packaging, cover panel 14 may be folded forward over backing panel 11 with release paper 15 interposed between the adhesive coatings, and matrix panels 12 and 13 folded to the rear of backing panel 11. The folded package is placed in a paper envelope or other enclosure and sterilized by ethylene oxide or radiation in accordance with established procedures for sterilizing surgical devices, with care being taken to select conditions which are not detrimental to the adhesive or the materials of construction of the receiver. Most preferably, the receiver is sterilized by exposure to ethylene oxide.

The adhesives useful in the present invention may be any of a number of well-known, transparent, nontoxic adhesive compositions. Pressure sensitive adhesive, i.e., adhesives which are inherently tacky, viscoelastic and cohesive in the normal dry state, and which are also nontoxic, nonirritating, and suitable for use in surgical, dermatological or cosmetic applications are known in the art. For example, representative materials suitable for use as adhesive coatings for surgical tapes as given in U.S. Pat. No. 3,645,835, incorporated herein by reference, include blends of vinyl ether or acrylic polymers, hydroxy acrylate polymers, polyvinyl ethyl ethers, and acrylate ester copolymers containing hydrophillic groups. Other suitable adhesives include rubber-based adhesives such as polyisobutylene and mixtures of polyisobutylene with natural rubber, and the rubbery copolymer of isoctyl acrylate and acrylic acid in a 94:6 ratio as described in U.S. Pat. Nos. 2,884,126 and 3,121,021, both of which patents are incorporated herein by reference. The transparent insert of the cover panel may be constructed of any polymeric film material which is sterilizable and transparent. Suitable materials include the lower polyolefinic polymers such as polyethylene and polypropylene and copolymers of ethylene and propylene, with high density polyethylene and polypropylene being particularly preferred. Other suitable polymers include nylon 6 and nylon 66, polyesters such as poly(ethylene terephthalate), acrylics such as polyacrylonitrile and copolymers of acrylonitrile and vinylacetate, polystyrene, and unplasticized polyvinyl chloride. These films may be surfce activated by corona discharge utilizing known techniques if necessary to make the surface receptive to coating with the adhesive.

The receivers of the present invention provide a convenient and inexpensive means for counting and disposing of surgical sharps. Many variations in the design and construction of the receiver will be apparent to those skilled in the art and the invention is accordingly not limited to the details of the specific embodiments disclosed herein. For example, a third matrix panel having a different window configuration from that of other matrix panels could be attached to the backing panel along the fourth side thereof, or the receiver could be provided with only one matrix panel already affixed to the backing panel and ready for use as illustrated in FIG. 2. Additionally, the transparent insert in the cover panel could be omitted with the consequence of being unable to view the contents of the receiver once the cover panel was closed. The entire receiver could also be constructed of thin plastic or plastic foam rather than paperboard as described above. Yet other variations will be apparent to those skilled in the art.

What is claimed is:

1. A receiver for disposing of surgical sharps comprising a backing panel, a cover panel attached along one edge of said backing panel, a first matrix panel attached along a second edge of said backing panel and a second matrix panel attached along a third edge of said backing panel, said cover and matrix panels having dimensions substantially corresponding to those of said backing panel and being adapted to fold along said edge of attachment to overlay said backing panel, said backing panel and said cover panel having a coating of a pressure-sensitive adhesive on one surface thereof, said matrix panels having a plurality of surgical sharp receiving windows therein and being readily detachable from said backing panel, wherein one matrix panel may be detached from said backing panel and discarded while the other matrix panel is folded over the adhesive coated surface of said backing panel and adhesively secured thereto to provide a plurality of surgical sharp receiving windows having an adhesive coated base surface.

2. A receiver of claim 1 wherein the windows of one matrix panel for fewer in number and larger in size than the windows in the other matrix panel.

3. A receiver of claim 1 wherein said cover panel has a transparent film insert over an area corresponding to the expanse of the windows in the matrix panel.

4. A receiver of claim 1 wherein said panels are constructed of paperboard.

5. A receiver of claim 1 wherein the line of attachment between said matrix panels and said backing panels is perforated.

6. A receiver of claim 1 wherein the adhesive coating on the cover panel is covered by a removable release paper.

7. A receiver of claim 1 wherein said first matrix panel has at least ten windows and said second panel has at least 20 windows.

8. A method for counting and disposing of surgical sharps comprising:
   a. providing a receiver according to claim 1;
   b. detaching one matrix panel from said backing panel and discarding said matrix panel;
   c. folding the other matrix panel over the adhesive coated surface of the backing panel and adhesively securing said matrix panel to said backing panel;
   d. depositing used surgical shaprs on the adhesive coating of the backing panel appearing through the windows of the matrix panel; and
   e. folding the adhesive coated cover panel over the matrix panel and adhesively securing said cover panel to said matrix panel, whereby said surgical sharps are enclosed between said backing panel and said cover panel within the windows of said matrix panel.

9. A method of claim 8 wherein one surgical sharp is deposited in each window of the matrix panel.

10. A method of claim 8 wherein the enclosed surgical sharps are visible through a transparent insert in the cover panel.

11. A method of claim 8 wherein more than one surgical sharp is deposited in each window of the matrix panel.

* * * * *